(12) United States Patent
Ellis et al.

(10) Patent No.: US 9,850,450 B2
(45) Date of Patent: Dec. 26, 2017

(54) INTERESTERIFICATION CATALYST AND PROCESS

(71) Applicant: JOHNSON MATTHEY PUBLIC LIMITED COMPANY, London (GB)

(72) Inventors: Peter Richard Ellis, Berkshire (GB); Gary Evans, Berkshire (GB); Aalbert Zwijnenburg, Doetinchem (NL)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 14/911,332

(22) PCT Filed: Aug. 15, 2014

(86) PCT No.: PCT/GB2014/052515
§ 371 (c)(1),
(2) Date: Feb. 10, 2016

(87) PCT Pub. No.: WO2015/028779
PCT Pub. Date: Mar. 5, 2015

(65) Prior Publication Data
US 2016/0201011 A1 Jul. 14, 2016

(30) Foreign Application Priority Data

Aug. 28, 2013 (GB) .................................. 1315276.4

(51) Int. Cl.

| | | |
|---|---|---|
| *C11C 3/10* | (2006.01) | |
| *B01J 35/02* | (2006.01) | |
| *B01J 35/10* | (2006.01) | |
| *C07C 67/02* | (2006.01) | |
| *B01J 37/03* | (2006.01) | |
| *B01J 23/00* | (2006.01) | |
| *B01J 23/02* | (2006.01) | |
| *B01J 23/04* | (2006.01) | |
| *B01J 23/34* | (2006.01) | |
| *B01J 37/04* | (2006.01) | |
| *B01J 37/08* | (2006.01) | |
| *B01J 33/00* | (2006.01) | |
| *B01J 37/00* | (2006.01) | |

(52) U.S. Cl.
CPC ............... *C11C 3/10* (2013.01); *B01J 23/002* (2013.01); *B01J 23/02* (2013.01); *B01J 23/04* (2013.01); *B01J 23/34* (2013.01); *B01J 35/023* (2013.01); *B01J 35/1009* (2013.01); *B01J 35/1014* (2013.01); *B01J 37/03* (2013.01); *B01J 37/035* (2013.01); *C07C 67/02* (2013.01); *B01J 33/00* (2013.01); *B01J 37/0045* (2013.01); *B01J 37/04* (2013.01); *B01J 37/08* (2013.01); *B01J 2523/00* (2013.01)

(58) Field of Classification Search
CPC ...................................................... C07C 67/02
See application file for complete search history.

(56) References Cited

U.S. PATENT DOCUMENTS 6,072,064 A 6/2000 Bayense et al.

FOREIGN PATENT DOCUMENTS

| CN | 101108350 | 1/2008 |
|---|---|---|
| CN | 102430400 | 5/2012 |
| FR | 1066898 | 6/1954 |
| JP | 2004-35873 A | 2/2004 |
| WO | 2009/143159 A1 | 11/2009 |
| WO | 2011/007362 A1 | 1/2011 |
| WO | WO2011007362 | 1/2011 |

OTHER PUBLICATIONS

"Dolomite, CaMg(CO3)2," 2000, Retrieved from the Internet: URL:http://rruff.info/doclib/hom/dolomite.pdf.
Georgogianni et al., "Transesterification of soybean frying oil to biodiesel using heterogeneous catalysts," Fuel Processing Technology, vol. 90, pp. 671-676, 2009.
Jitputti et al., "Transesterification of crude palm kernel oil and crude coconut oil by different solid catalysts," Chemical Engineering Journal, vol. 116, pp. 61-66, 2006.
Yan et al., "Simultaneous transesterification and esterification of unrefined or waste oils over ZnO-La2O3 catalysts," Applied Catalysts A: General, vol. 353, pp. 203-212, 2009.

*Primary Examiner* — Yate K Cutliff
(74) *Attorney, Agent, or Firm* — Baker & Hostetler LLP

(57) ABSTRACT

A process for the production of an ester product from a mixture of at least two different ester compounds includes the steps of mixing together at least two different starting ester compounds to form a first ester mixture; and contacting the first ester mixture with a catalyst including from 30-60% of calcium oxide and at least one second metal oxide at a temperature of at least 180° C., for a duration of at least one hour, with mixing, to form a second ester mixture having a melting point which is lower than the melting point of the first ester mixture.

12 Claims, No Drawings

INTERESTERIFICATION CATALYST AND PROCESS

The present invention concerns catalysts for use in chemical transformations, in particular for use in esterification processes useful for the production of edible fats and oils.

Hydrogenation, fractionation and interesterification are processes that can be used to modify the properties of edible oils, and thus make them suitable for use in a wider range of products and applications. Hydrogenation has traditionally been the most popular method, however partial hydrogenation of triglycerides can lead to unwanted side reactions and these result in the formation of trans isomers of the constituent fatty acids. These so-called trans fats have been linked to a variety of human health problems including coronary heart disease.

Interesterification is a process whereby acyl groups are transferred between esters, such as triglyceride molecules, in the presence of a catalyst. It is typically performed with a mixture of oils; one saturated and one unsaturated, in the presence of a catalyst such as sodium methoxide. It is an attractive alternative to hydrogenation as it does not involve chemical modification of the fatty acid chains, and so no trans isomers are produced. A number of problems arise from the use of sodium methoxide; for example it is not possible to recover the catalyst after the reaction and a significant amount of waste water is produced during its removal from the oil. In addition, sodium methoxide is very sensitive to free fatty acids and water, meaning the reaction can only be performed in highly refined feedstocks otherwise ester hydrolysis and soap formation (saponification) can occur.

The use of a heterogeneous catalyst for this process would overcome some of the problems with sodium methoxide because the catalyst would be more easily recoverable from the reaction products. U.S. Pat. No. 6,072,064 describes the use of heterogeneous catalysts comprising mixtures of Group 1A and Group 2A metal oxides for the catalytic interesterification of triglycerides, wherein at least one of the oxides has an optical basicity of at least 0.5. Whilst these catalysts appear to be effective, we have found that they are liable to form metal soaps during the course of the reaction and that their reusability suffers as a result. It is an object of the invention to provide a catalyst and interesterification process that overcomes some of the problems encountered in the prior art.

According to the invention, we provide a catalyst comprising 30-60% by weight (wt %) of calcium oxide and 40-70% by weight of magnesium oxide.

A process, according to the invention, for the production of an ester product from a mixture of at least two different ester compounds comprises the steps of:
a) mixing together at least two different starting ester compounds to form a first ester mixture; and
b) contacting said first ester mixture with a catalyst comprising from 30-60% of calcium oxide and at least one second metal oxide, to form a second ester mixture having a melting point which is lower than the melting point of said first ester mixture.

The process of the invention is an interesterification process, wherein the acyl group of one ester exchanges with the acyl group of a different ester to form two esters which are different from the starting two esters. When at least one of the starting esters is a triglyceride, interesterification produces a product triglyceride having carbonyl-residue chains which differ from the triglyceride chains of the starting esters, resulting in a product having a different melting point compared with the starting material. In a preferred process of the invention at least one of the starting ester compounds comprises a triglyceride which is preferably a vegetable oil or animal fat or derivative thereof. Preferably at least one of the starting ester compounds comprises an ester of a C12-C24 carboxylic acid. Suitable starting materials include palm oil, soybean oil palm kernel oil, stearins such as palm kernel stearin, olein, such as palm kernel olein, coconut oils, fish oils and derivatives thereof.

Interesterification requires at least two different ester starting compounds although more than two esters may be used. The at least two starting esters may be mixed prior to contact with the catalyst or during said contact. For example, the catalyst may be mixed with one or more of the starting ester compounds before mixing with other ester compounds. In particular the catalyst may be pre-dispersed in one starting ester compound. In this form, the ester compound in which the catalyst is dispersed is preferably a solid material at a temperature up to at least 40-50° C. so that the catalyst may be protected from contact with air prior to use in the reaction. Encapsulation of catalyst particles or powders by dispersal in a fatty or waxy solid is a known method of protecting catalysts particularly catalysts used in the processing of edible oils and fats. In this case, for use in the process of the invention, the encapsulating substance preferably comprises a starting ester compound.

All percentages of catalyst constituents in this patent specification refer to % by weight (wt %), based on the total mass of the catalyst, unless stated otherwise. The catalyst used in the process of the invention comprises from 30-60 wt % of calcium oxide, more preferably 35-55 wt % of calcium oxide. The catalyst further comprises at least one second metal oxide, preferably from 40-70% of said second metal oxide. Suitable second metal oxides include oxides of other Group 2A metals, particularly magnesium; oxides of transition metals such as manganese and zirconium; lanthana, silica, alumina and aluminates, such as lithium aluminate. A preferred catalyst for use in the process of the invention comprises from 30-60% of calcium oxide and 40-70% of magnesium oxide. The catalyst may consist of or consist essentially of calcium oxide and magnesium oxide and optional ingredients selected from an alkali metal, pelleting aids, lubricants, binders, compaction aids or other additives useful in forming a shaped catalyst particle. CN101108350 describes a catalyst for steam reforming of syngas in which a core support particle is formed from a composite of calcium oxide, magnesium oxide and alumina which is then coated with lanthanum aluminate and used as a catalyst support for a nickel and rare earth catalyst. The catalyst of the present invention does not include such catalysts in which calcium oxide and magnesium oxide are used to form a core, support or carrier, whether coated or uncoated, onto which an active metal such as nickel and rare earth is deposited. The catalyst of the invention comprises 30-60% of calcium oxide and from 40-70% of magnesium oxide as active catalytic components.

The catalyst may additionally comprise an alkali metal, preferably sodium or potassium. We have found that catalysts containing up to 5% alkali metal may be advantageous. A particularly preferred catalyst for use in the process of the invention comprises, or consists essentially of, 30-60% of calcium oxide, 40-70% of magnesium oxide and optionally up to 5% sodium or potassium.

For use in the interesterification of fatty esters, the catalyst preferably has a surface area less than 20 m$^2$/g, more preferably ≤10 m$^2$/g, especially ≤5 m$^2$/g. We have found that greater surface areas may increase the tendency to form metal soaps in the reaction. In order to produce a catalyst of acceptable activity, we prefer that the surface area is at least 1 $m^2$/g, more preferably at least 2 $m^2$/g.

The catalyst may be made by various different methods of the type generally used in the art of catalyst manufacture. Such methods include impregnation and precipitation. Calcium oxide is a solid material which combines with water and carbon dioxide to form calcium carbonate and calcium hydroxide. In order to form a material comprising a high proportion of calcium oxide, it is necessary to treat calcium oxide or a precursor thereof (for example calcium nitrate, carbonate, acetate or hydroxide) at a temperature of at least 650° C. (preferably above 700° C.) in the absence of oxygen and carbon dioxide for sufficient time to wholly or partially convert the precursor or other calcium compounds to calcium oxide. The calcium oxide thus formed should then be cooled and stored without contact with oxygen and carbon dioxide. The catalyst may be prepared by impregnation, to impregnate solid particles of the second metal oxide with a solution of a precursor of calcium oxide. Alternatively, a solid precursor of calcium oxide may be impregnated with a solution of a precursor of the second metal oxide. By precursor, we mean a compound of calcium or the second metal which is transformed to the oxide by the application of heat. Suitable precursors, including calcium nitrate, magnesium nitrate and organic salts such as calcium acetate, are soluble in water to produce an aqueous solution for impregnation.

The catalyst may be prepared by precipitation in different ways. In each case, a solution of a soluble calcium compound is used to precipitate a solid precursor of the calcium oxide. For example, a solution of calcium nitrate or calcium acetate may be mixed with a solution of a base, such as an alkali metal carbonate or hydroxide to precipitate calcium hydroxide or calcium carbonate. The precipitated solid calcium compound is transformed to calcium oxide in a calcination step. The catalyst may be made by co-precipitation of the precursor calcium compound with a precursor to the second metal oxide. In this method, solutions of soluble precursor compounds of calcium and of the second metal, for example magnesium nitrate, are contacted together with the base solution to precipitate a mixture of the basic salts of calcium and the second metal. Alternatively a deposition-precipitation method may be used, in which a solution of the soluble calcium precursor is contacted with the solution of base in the presence of solid particles of the second metal oxide (or a solid precursor thereof). By solid precursor, we mean a solid compound which is transformed to the second metal oxide by the action of heat. The transformation normally takes place in a calcination step. All of these precipitation methods are generally known and used in the art of catalyst preparation.

Alternatively, the catalyst may be prepared by mixing together solid particles of calcium oxide, or a solid precursor thereof, with solid particles of the second metal oxide, or a solid precursor thereof. We have found that an effective preparation method includes the steps of mixing together solid particles of calcium oxide, or a solid precursor thereof, with solid particles of the second metal oxide, or a solid precursor thereof, with a liquid to form a slurry which is then dried to form particles of the mixed solids. It is preferred to use a rapid drying method such as spray-drying or freeze-drying in this method of manufacture. The resulting solid compounds are then converted to the oxides in a calcination step. The slurry of solid calcium and second metal compounds may optionally be subjected to mechanical energy in a milling, grinding or energetic mixing process prior to drying the mixture.

As a still further alternative catalyst preparation method, a solution containing soluble precursors of the calcium compound and second metal compound may be dried to form a mixed solid. A rapid drying method such as spray-drying or freeze drying is conveniently used in this method. The resulting solid compounds are then converted to the oxides in a calcination step.

The catalyst may be used in the form of a powder in a slurry-phase process or it may be formed into particles suitable for use in a fixed bed reactor. For use in slurry phase processes it is preferred to provide catalyst particles having a particle size distribution such that d50 lies in the range 0.5-50 microns, especially 10-40 microns. An important consideration for slurry-phase processes is that the particles must be separated from the reaction products when the reaction is complete. Separation is normally accomplished by filtration and therefore the particles should be of such a particle size and particle size distribution to enable rapid and complete filtration from the reaction medium.

The catalyst of the invention may comprise shaped particles which are suitable for use in catalyst beds, i.e. so called "fixed bed" processes. Such particles generally have a minimum dimension greater than about 0.5 mm, especially greater than about 1 mm and may range in size from 1 mm to 50 mm or greater. Fixed bed catalyst particles may have a variety of shapes including spheres, rings, cylinders, lobed cylinders, pellets, tablets etc and may be formed by tabletting, extrusion, granulation, coating onto cores or other forms of moulding by methods known to the skilled person. The process of forming the catalyst into shaped particles may include compaction and/or pre-compaction steps. A pre-compaction step may be useful to improve the flow characteristics of catalyst powders for use in a forming process. The forming process may include grinding, rolling, pressing, milling, sieving and/or mixing steps. Binders, lubricants, compaction aids or other additives may be added to or mixed with a catalyst for forming into shaped catalyst particles. For example a binder may be added at an amount equivalent to about 0.1-10% by weight, for example about 1% by weight. Examples of suitable binders include magnesium stearate and graphite.

The interesterification reaction preferably takes place at a temperature between 0 and 300° C., more preferably between 150 and 250° C., especially 200-250° C. The reaction has been found to operate well under atmospheric pressure and would be expected to operate at pressures at slightly raised or reduced pressure also. When the reaction is for the interesterification of edible oils and fats, it is desirable to avoid the exposure of the ester starting materials and products to conditions which lead to oxidation of the triglycerides. This may involve conducting the reaction under reduced pressure, and/or a non-oxidising atmosphere or changing the temperature to reduce the likelihood of oxidation. Other feedstocks and products may require different reaction conditions to be maintained. Liquid-phase processes may take place under trickle-bed conditions, usually at LHSV values up to about 2, for example about 1.

It is a particular advantage of the catalysts of the invention that they maintain their activity and can be re-used after withdrawal from a batch reaction or have a long period of active use in a continuous process. The interaction of metal catalysts with fatty acids and esters tends to lead to the formation of metal soaps. Metal soaps are disadvantageous because they are not catalytically active so their formation involves the loss of metal catalyst from the reaction. Furthermore they can be difficult to separate from the reaction products and, if separable, tend to stick to parts of the process apparatus which may result in a reduction in the efficiency of filtration systems, for example. We have found that the catalysts of the invention, when used in an interesterification process of the invention have a reduced tendency to form metal soaps compared with prior art catalysts and therefore have a longer period of activity. For example, we have found that a CaO—MgO catalyst of the invention can be used for five consecutive interesterification reactions without any significant effect on the reaction product. This leads to significant commercial and environmental benefits because the catalyst need not be replaced so frequently. A reduced tendency to form metal soaps in fatty ester reactions also leads to processing advantages for the operator.

The invention will be further described in the following examples.

EXAMPLE 1

17.70 g of $Ca(NO_3)_2.4H_2O$ and 18.81 g of $Mn(NO_3)_2.4H_2O$ were dissolved in 273 mL of demineralised $H_2O$. In addition, 28.6 g of $Na_2CO_3$ (anhydrous) was dissolved in 337 mL of demineralised $H_2O$, and this solution was heated to 60° C. while stirring at 600 rpm. The solution containing the calcium and manganese salts was then added to the $Na_2CO_3$ solution in a drop-wise manner, which lead to the immediate formation of a light brown-coloured precipitate. After the completion of metal salt addition the reaction was left stirring at 60° C. for 1 hour. The precipitate was then collected by filtration and re-dispersed in hot water. This procedure was performed in order to remove as much of the residual sodium from the sample as possible. The precipitate was re-collected and the washing step was repeated a further two times, before the precursor was dried overnight at 80° C.

Thermogravimetric analysis (TGA) performed using a TA Instruments SDT2960 instrument showed a major mass loss at around 725° C., suggesting oxide formation at this temperature. Samples were subsequently calcined at 800° C. for 2 hours in air.

X-ray diffraction (XRD) spectra, collected using a Bruker D8 Advance instrument with a Cu source, showed the calcined material consisted of phase-pure perovskite.

Inductively coupled plasma atomic emission spectroscopy (ICP-AES), run on a Perkin Elmer Optima 3300 RL instrument, showed 28.4% Ca, 38.8% Mn and 1.8% Na. BET surface area data, collected on a Quantachrome Autosorb-1 instrument, gave a surface area of 2.3 $m^2/g$.

The analytical methods described in this Example were used to characterise the materials made in the subsequent examples, unless stated otherwise. All catalysts were stored in an argon atmosphere in a glove-box prior to use or characterisation.

EXAMPLE 2

A material was prepared using the same procedures as in Example 1 except that 10.6 g $Sr(NO_3)_2$ and 12.57 g of $Mn(NO_3)_2.4H_2O$ were dissolved in 273 mL $H_2O$ and 19.1 g $Na_2CO_3$ was dissolved in 225 mL $H_2O$. XRD showed the calcined material was comprised predominantly of the perovskite phase $SrMnO_3$ with a small amount of $SrCO_3$ present. ICP-AES data showed the material 43.4% Sr, 29.7% Mn and 1% Na. The BET surface area was 2.6 $m^2/g$.

EXAMPLE 3

20.8 g calcium acetate monohydrate was dissolved in 131.5 mL $H_2O$ and this solution was added to 10 g magnesium oxide powder (Sigma Aldrich, surface area 72.2 $m^2/g$). The resulting slurry was stirred and heated at 80° C. until dry and then further dried at 80° C. overnight. The TGA data showed several mass losses, with the loss in mass appearing to end after 650° C. The sample was calcined at 780° C. for 8 hours and XRD showed the material consisted of crystalline CaO and MgO. ICP-AES gave the expected amounts of Ca and Mg, 24.3 and 30.6% respectively. A BET surface area of 10.7 $m^2/g$ was recorded. The overall loading of CaO was equal to 40 wt % (wt CaO/(wt CaO+wt MgO)).

EXAMPLE 4

11.8 g of $Ca(NO_3)_2.4H_2O$ and 26.93 g of $Mg(NO_3)_2.6H_2O$ were dissolved in 1 L of $H_2O$. A second solution contained 29.53 g of $Na_2CO_3$ dissolved in 1 L $H_2O$. The concentrations of the solutions were therefore 0.1550 M (metal) and 0.2786 M (base). Both solutions were heated to 60° C. while being magnetically stirred and then the solutions were pumped into a flash precipitation reactor at 20 mL/min, with stirring inside the reactor set to 2000 rpm. The resulting mixture was collected and kept at room temperature for 1 day. The precipitate was collected by filtration, re-slurried, washed with warm water and filtered again. This washing procedure was performed a further 3 times before the precipitate was dried at 80° C. overnight. The dried powder was calcined in air at 800° C. for 2 hours inside a tube furnace and then cooled to room temperature under a flow of argon to avoid the formation of bulk carbonate and the adsorption of $CO_2$ to the catalyst surface.

XRD showed a phase-pure CaO—MgO material with no $CaCO_3$. ICP-AES analysis showed 34.2% Ca, 31.7% Mg and 0.4% Na. The BET surface area was 12.6 $m^2/g$.

EXAMPLE 5

A material was prepared in the same manner as and with the same quantities as described in Example 4, however the calcium and magnesium nitrate salt solution was added drop-wise into a magnetically stirred sodium carbonate solution. Upon completion of addition the precipitate was aged for 1 hour at 60° C. and then filtered, re-slurried in warm water and re-filtered. The filtration process was repeated a further 3 times, after which the precipitate was then aged at 80° C. overnight. Calcination was performed in a tube furnace under flow of air at 800° C. for 2 hours with the sample then cooled to room temperature under Ar. ICP-AES analysis showed 33.6% Ca, 30.8% Mg and 0.6% Na. The BET surface area was 12.7 $m^2/g$.

EXAMPLES 6-8

Materials were prepared using the method described in Example 5 using different amounts of calcium nitrate and sodium carbonate while maintaining the same overall metal concentration. Materials containing 30 wt % CaO, 50 wt % CaO and 60 wt % CaO were prepared by this method which had measured surface areas of 54.3 $m^2/g$, 7.9 $m^2/g$ and 6.7 $m^2/g$ respectively.

EXAMPLE 9

A material containing 40 wt % CaO and MgO was also prepared as described in Example 5, by freeze drying instead of standard drying. A surface area of 49.5 m$^2$/g was measured using the BET method.

EXAMPLE 10-11

Materials containing 40 wt % and 50 wt % CaO, respectively, were prepared using the general method described in Example 5 except that the solids concentration was increased four times by doubling the required amounts of calcium nitrate, magnesium nitrate and sodium carbonate and halving the amount of water. Surface areas of 18.6 m$^2$/g (40 wt % CaO) and 9.0 m$^2$/g (50 wt % CaO) were recorded using the BET method.

EXAMPLE 12

Calcium carbonate was deposited by precipitation onto a pre-formed MgO support as follows: 10 g of MgO (heavy, BDH Chemicals) was dispersed in 192 mL of H$_2$O, to which 22.66 g of Na$_2$CO$_3$ was added. This dispersion was heated to 60° C. A solution was made consisting of 28.07 g of calcium nitrate tetrahydrate in 192 mL of H$_2$O and this solution was added to the MgO dispersion in a dropwise manner with stirring. Formation of a white precipitate was observed on addition, and this was left stirring at 60° C. for 1 hour. The solids were collected by vacuum filtration and washed with warm water (250 mL) a total of 4 times by re-slurrying and filtering. The washed solids were then dried overnight at 80° C. and calcined in air (800° C. for 2 hours, 10° C./min ramp rate) with cooling under a flow of Ar. A surface area of 4.8 m$^2$/g was recorded using the BET method, while ICP-AES showed 29.5% Ca, 33.9% Mg and 0.69% Na.

EXAMPLES 13-18

Materials having the same nominal 40 wt % CaO loading were prepared using, instead of the heavy MgO solid material, MgO (light, from Alfa Aesar)), LiAlO$_2$ (supplied by Alfa Aesar), ZrO$_2$, SiO$_2$ (P432), Al$_2$O$_3$ (PURALOX™ HP14/150) and La$_2$O$_3$ (prepared by precipitating lanthanum carbonate precursor from lanthanum nitrate using sodium carbonate, followed by calcination).

EXAMPLE 19

A material was prepared by mixing 11.9 g of CaCO$_3$ and 10 g of MgO (light, Alfa Aesar) in 500 mL H$_2$O (solid concentration of 0.044 g/mL). The mixture of suspended particles was then spray dried using a Buchi B-290 Mini Spray Drier at a rate of 15 mL/min with an inlet temperature of 180° C. and an air flow rate of 670 L/hour. The spray dried powder was calcined in air at 800° C. for 2 hours inside a tube furnace and then cooled to room temperature under a flow of argon.

EXAMPLES 20-23

Materials containing 40% CaO and either 0.5, 1, 2 or 5 wt % sodium, respectively, were prepared by the method described in Example 19 by adding sodium carbonate to the calcium and magnesium mixture. 0.3842 g Na$_2$CO$_3$ was used to provide 1% sodium in the final material and other concentrations of sodium were made by modifying the amount of sodium carbonate added.

EXAMPLE 24

A material containing 40% CaO and 2% sodium was prepared using the method of Example 22 but using a calcination temperature of 715° C. The surface area of the final catalyst was 19.5 m$^2$/g.

EXAMPLES 25-29

Materials containing 40% CaO and either 0, 0.5, 1, 2 or 5 wt % sodium, respectively, were prepared by the method described in Examples 19-23 but using a dispersion of LiAlO$_2$ (Alfa Aesar) instead of MgO.

EXAMPLE 30

A material containing 40% CaO and 2% sodium was prepared using the method of Example 22 with the addition of a wet-milling step prior to spray drying. The powders were dispersed in 50 mL H$_2$O and milled using a Fritsch Pulverisette planetary ball mill with 10 mm ZrO$_2$ beads at a 1:10 powder to beads mass ratio, at 400 rpm for 1 hour, with 10 minute pauses after every 15 minutes. The mixture was then made up to 500 mL with water and spray dried as in Example 19. A surface area of 9.8 m$^2$/g was recorded for the calcined material.

EXAMPLE 31

A material was prepared by spray drying an aqueous solution of calcium, magnesium and sodium acetates. 30 g magnesium acetate tetrahydrate, 11.82 g calcium acetate monohydrate and 1.11 g sodium acetate trihydrate were dissolved in 300 mL water. The resulting solution was spray dried at a rate of 9 mL/min with an inlet temperature of 130° C. and an air flow rate of 670 L/hour. The powder was then calcined in a tube furnace in air at 800° C. for 2 hours. The furnace was ramped at 10° C./min to 300° C., then at 5° C./min to 400° C. and again at 10° C./min to 800° C., before being allowed to cool under a flow of argon. A BET surface area of 6.5 m$^2$/g was recorded.

COMPARATIVE EXAMPLE A

An interesterification catalyst comprising K$_2$CO$_3$ and MgO was prepared. 5 g of K$_2$CO$_3$ was dissolved in 17 mL H$_2$O and added to 19.84 g of MgO. The catalyst was dried overnight at room temperature and then at 110° C. for 16 hours. Calcination was performed at 500° C. for 2 hours in air. This procedure is intended to produce a catalyst as described in Example 3 of U.S. Pat. No. 6,072,064 for the purpose of comparison.

EXAMPLE 32: INTERESTERIFICATION REACTION

The materials made as described in Examples 1-31 were tested as interesterification catalysts. A slurry-phase interesterification reaction was performed using the powdered catalyst under the following conditions:

Raw materials: soybean oil and palm stearin at a weight ratio 4:1, (12.5 g of soybean oil and 3.125 g palm stearin).
Amount of catalyst: 10 wt %, (1.57 g)
Reaction temperature: set temperature 225° C., giving an oil temperature of 205° C.
Reaction time: 5 hours
Pressure: atmospheric pressure
Stirring rate: set to 600 rpm Atmosphere: reactions performed under a flow of argon gas, to avoid oxidation of the oils. Samples of the oil were taken at 1 hour intervals and these were analysed by differential scanning calorimetry (DSC) using a Mettler Toledo DSC822e instrument from −60° C. to 60° C. The activity of the catalyst was assessed by determining the partial areas under the DSC peak(s) and, by assuming the oil was 100% solid at −60° C., and 0% solid at 60° C., it was possible to determine the percentage of oil that was solid at a particular temperature T. The melting point was considered to be the temperature at which the oil was 5% solid and 95% liquid. The activity of each catalyst may then be compared by comparing the melting point of the oil mixture following reaction. The starting soybean oil and palm stearin mixture has a melting point of 51.5° C. measured by this method and this drops to 30.9° C. following interesterification using sodium methoxide. The results are shown in Table 1.

COMPARATIVE EXAMPLE B

Sulphated tin oxide ($SnO_2$—$SO_4^{2-}$) was prepared as according to the method described by Jitputti et al (J. Jitputti, B. Kitiyanan, P. Rangsunvigit, K. Bunyakiat, A. Attanatho, P. Jenvanitpanjakul, Chem. Eng. J., 2006, 116, 61). This reference describes the promising activity of this material for the transesterification of triglycerides with methanol. The sample was tested for the interesterification of soybean oil and palm stearin as described in Example 32. No change was found in the melting properties of the oils after the reaction indicating that Comparative Example B showed no activity as an interesterification catalyst.

COMPARATIVE EXAMPLE C

Sulphated zirconium oxide ($ZrO_2$—$SO_4^{2-}$) was prepared as according to the method described by Jitputti et al (J. Jitputti, B. Kitiyanan, P. Rangsunvigit, K. Bunyakiat, A. Attanatho, P. Jenvanitpanjakul, Chem. Eng. J., 2006, 116, 61). The samples was tested for the interesterification of soybean oil and palm stearin as described in Example 32. No change was found in the melting properties of the oils after the reaction indicating that Comparative Example C showed no activity as an interesterification catalyst.

COMPARATIVE EXAMPLE D

According to the publications of S. Yan et al, (S. Yan, S. O. Salley, K. Y. S. Ng, Appl. Catal. A, 2009, 353, 203), $ZnO$—$La_2O_3$ is a highly active catalyst for the transesterification of triglycerides and methanol to fatty acid methyl esters and glycerol. Samples of '$ZnO$—$La_2O_3$' (shown by XRD in both the referenced publication and our own work to be comprised of a mixture of lanthanum phases, primarily $La_2O_2CO_3$) at Zn/La ratios of 3:1 and 6:1 were prepared according to the method described by the authors. The samples were tested in the interesterification process according to Example 32 and showed no activity, with the melting point recorded at 51.1° C. before and after the reaction.

COMPARATIVE EXAMPLE E

Georgogianni et al. (K. G. Georgogianni, A. P. Katsoulidis, P. J. Pomonis, M. G. Kontominas, Fuel Process. Technol., 2009, 90, 671) describes several mixed oxide systems for the transesterification of soybean oil with methanol. The Mg—Al hydrotalcite (Mg/Al ratio of 3:1) was found to be the most basic and most active of their materials, achieving a 96% conversion of soybean oil to fatty acid methyl esters under their reaction conditions. We prepared the Mg—Al hydrotalcite catalyst according to the description in the referenced journal article at the Mg/Al ratio of 3:1. The catalyst showed no activity for the interesterification process described by Example 32, with the oil melting point remaining unchanged at 51.5° C. after the reaction.

Comparison Examples B-E show that catalysts which have previously been demonstrated to be active for transesterification may not be useful interesterification catalysts.

EXAMPLE 33

The amount of catalyst metal leaching from the catalyst into the oil during interesterification was determined by analysing the product oil by ICP-AES following removal of the catalyst after the reaction. The results are shown in Table 2.

TABLE 2

|  | Ca (ppm) | Mn (ppm) | Na (ppm) | Mg (ppm) |
|---|---|---|---|---|
| Oil before interesterification | 30 | <10 | <10 |  |
| Oil after interesterification Catalyst 1 | 14 | 133 | 19 |  |
| Oil after interesterification Catalyst 5 | 30 |  | <10 | <10 |

This shows that the CaO—MgO catalyst has superior resistance to metal leaching compared with the $CaMnO_3$ catalyst. This is a particular advantage because the presence of metal species in edible oils is generally undesirable.

TABLE 1

| Catalyst Example | Catalyst type | CaO (wt %) | Other comments | Surface area (m²/g) | Melting point (° C.) |
|---|---|---|---|---|---|
| 1 | $CaMnO_3$ |  | 28.4% Ca | 2.3 | 30.9 |
| 2 | $SrMnO_3$ | — | 43.4% Sr | 2.6 | 36.7 |
| 3 | CaO—MgO | 40 |  | 10.7 | 43.8 |
| 4 | CaO—MgO | 40 |  | 12.6 | 32.9 |
| 5 | CaO—MgO | 40 |  | 12.7 | 33.4 |
| 6 | CaO—MgO | 30 |  | 54.3 | 43.6 |
| 7 | CaO—MgO | 50 |  | 7.9 | 34.5 |
| 8 | CaO—MgO | 60 |  | 6.7 | 37.6 |
| 9 | CaO—MgO | 40 |  | 49.5 | 37.8 |
| 10 | CaO—MgO | 40 |  | 18.6 | 33.1 |
| 11 | CaO—MgO | 50 |  | 9.0 | 35.7 |
| 12 | CaO—MgO | 40 |  | 4.8 | 34.6 |
| 13 | CaO—MgO | 40 | Light MgO | 4.2 | 34.9 |
| 14 | CaO—$LiAlO_2$ | 40 |  | 15.9 | 34.7 |
| 15 | CaO—$ZrO_2$ | 40 |  | 10.1 | 35.3 |
| 16 | CaO—$SiO_2$ | 40 |  | 27.7 | 46.5 |
| 17 | CaO—$Al_2O_3$ | 40 |  | 77.9 | 42.4 |
| 18 | CaO—$La_2O_3$ | 40 |  | 3.7 | 38.0 |
| 19 | CaO—MgO | 40 |  | 7.9 | 41.3 |
| 20 | CaO—MgO | 40 | 0.5% Na | 5.0 | 37.9 |
| 21 | CaO—MgO | 40 | 1.% Na |  | 37.8 |
| 22 | CaO—MgO | 40 | 2% Na | 2.6 | 33.2 |
| 23 | CaO—MgO | 40 | 5% Na | 5.1 | 31.6 |
| 24 | CaO—MgO | 40 | 2% Na | 19.5 | 32.1 |
| 25 | CaO—$LiAlO_2$ | 40 |  | 5.5 | 38.9 |
| 26 | CaO—$LiAlO_2$ | 40 | 0.5% Na |  | 37.3 |
| 27 | CaO—$LiAlO_2$ | 40 | 1.% Na |  | 36.6 |
| 28 | CaO—$LiAlO_2$ | 40 | 2% Na | 2.4 | 37.7 |
| 29 | CaO—$LiAlO_2$ | 40 | 5% Na | 1.9 | 36.6 |
| 30 | CaO—MgO | 40 | 2% Na | 9.8 | 34.0 |

TABLE 1-continued

| Catalyst Example | Catalyst type | CaO (wt %) | Other comments | Surface area (m²/g) | Melting point (° C.) |
|---|---|---|---|---|---|
| 31 | CaO—MgO | 40 | 2% Na | 6.5 | 32.9 |
| Comp A | $K_2CO_3$—MgO | | *2% catalyst loading | | 32.9 |

*Catalyst testing of Comparative Example A was performed as described except that the catalyst loading was 2 wt % and the reaction time was 1 hour.

EXAMPLE 34

Catalyst samples were collected after use in the interesterification reaction and used in four further interesterification reactions, being separated from the oil mixture each time before use in a subsequent reaction. The melting points after 5 hours of reaction time for each use or "cycle" are shown in Table 3. The catalyst Comparison A was used at 2% catalyst loading and the reaction time was 1 hour, as described above.

Examination of catalyst of Comparison Example A withdrawn from the first reaction cycle showed it to be associated with a waxy mixture of catalyst and metal soap material. The loss of metal to soap formation may explain the reduced activity of the catalyst in subsequent cycles. The catalyst of Example 5 also showed some evidence of soap formation after cycle 3. Soap formation was not observed in the catalyst of Example 22 until after cycle 5. Soaps were noticed in the Example 30 reactions during cycle 4 and the test was stopped for that reason.

TABLE 3

| Catalyst | MP Cycle 1 (° C.) | MP Cycle 2 (° C.) | MP Cycle 3 (° C.) | MP Cycle 4 (° C.) | MP Cycle 5 (° C.) |
|---|---|---|---|---|---|
| Example 5 | 33.4 | 32.0 | 30.0 | | |
| Example 22 | 33.2 | 33.1 | 33.3 | 32.9 | 32.8 |
| Example 30 | 34.8 | 34.3 | 34.9 | 32.6 | |
| Example 31 | 32.9 | 32.8 | 31.8 | 32.7 | |
| Example 37* | 33.0 | 33.1 | 35.5 | 40.3 | 43.5 |
| Comparison Example A | 32.9 | 35.7 | 38.5 | 42.3 | 46.2 |

*Note: 90 minute reaction time

EXAMPLE 35 (COMPARISON)

Calcium carbonate was precipitated from a solution of calcium nitrate using a solution of ammonium carbonate as the base solution. The solids were separated by filtration, washed and dried and calcined at 800° C. to convert them to calcium oxide. The calcium oxide solids were used as a catalyst in the interesterification reaction described in Example 32. After 5 hours the melting point of the reaction mixture was 47.1° C.

EXAMPLE 36 (COMPARISON)

Particles of magnesium oxide, of the type used in the preparation of Example 12 were used as a catalyst in the interesterification reaction described in Example 32. After 5 hours the melting point of the reaction mixture was 48.2° C.

EXAMPLE 37

A material was prepared by mixing 11.9 g of $CaCO_3$ and 10 g of MgO (light, Alfa Aesar) and 1 g of $K_2CO_3$ in 500 mL $H_2O$ (solid concentration of 0.044 g/mL). The mixture was calculated to give the same no of moles of K in the mixture as the number of moles of Na in Example 22. The mixture of suspended particles was then spray dried using a Buchi B-290 Mini Spray Drier at a rate of 15 mL/min with an inlet temperature of 180° C. and an air flow rate of 670 L/hour. The spray dried powder was calcined in air at 800° C. for 2 hours inside a tube furnace and then cooled to room temperature under a flow of argon.

The catalyst was tested in the interesterification reaction as described in Example 32, except that the reaction was run for only 90 minutes instead of for 5 hours. The catalyst was then collected and re-used in subsequent interesterification reactions (each 90 minutes) as described in Example 34. The melting point of the mixture after each cycle is shown in Table 3.

EXAMPLE 38

The spray dried catalyst described by Example 22 was formed into pellets. The CaO—MgO powder formed as described in Example 22 was mixed in a Turbula® shaker-mixer with 1 wt % graphite as binder. The mixture was compressed using an Alexanderwerk® Roller Compactor WP120 hydraulic press. The compacted material was then ground and sieved to achieve a size distribution of 250-600 microns, and mixed again in the shaker mixer with 1 wt % graphite. The mixture was then compressed into cylindrical tablets of 3 mm diameter and 3.3 mm length using a Dott Bonapace® CPR-6 hydraulic press. The tablets had an average density of 2.35 g/cm³ and an average crush strength (applied along the length of the pellet) of 6.5 kgf.

The catalyst pellets were tested in a Harshaw Falling Basket Catalyst Reactor using a high temperature bolted closure stirred batch reactor made by Autoclave Engineers. The test was performed as follows: 16.2 g (12 mL) of catalyst pellets were loaded evenly into four sample baskets. The autoclave was filled with the feedstock, comprising 360 g (400 mL) soybean oil and 90 g (100 mL) palm stearin. The system was held at 0.1 bar gauge pressure, which was the lowest measurable pressure for the system, with a flow of $N_2$ maintained through the reactor for the duration of the test. The autoclave was heated to 100° C. to melt the oil, and the reactor was then stirred at 250 rpm. The autoclave was then heated to 210° C. at which point the catalyst basket was dropped into the oil and the reaction begun. The reaction was stopped after 24 hours and the melting point of the oil was determined by DSC to be 36.3° C. at an equivalent LHSV of 1.74 $hr^{-1}$.

The invention claimed is:

1. An interesterification process for the production of an ester product from a mixture of at least two different ester compounds comprises the steps of:
    a) mixing together at least two different starting ester compounds to form a first ester mixture; and
    b) contacting said first ester mixture with a catalyst comprising from 30-60 weight % of calcium oxide and at least one second metal oxide such that an interesterification reaction takes place to form a second ester mixture having a melting point which is lower than the melting point of said first ester mixture, said second metal oxide is selected from the group consisting of an oxide of a Group 2A metal other than calcium, an oxide of a transition metal, lanthana, silica, alumina and a metal aluminate.

2. The interesterification process as claimed in claim 1, wherein at least one of said at least two different starting ester compounds is a triglyceride.

3. The interesterification process as claimed in claim 1, wherein at least one of the starting ester compounds comprises an ester of a carboxylic acid containing from 12 to 24 carbon atoms.

4. The interesterification process as claimed in claim 1, wherein the catalyst is pre-dispersed in at least one of said starting ester compounds.

5. The interesterification process as claimed in claim 1, wherein the second metal oxide comprises magnesium oxide.

6. The interesterification process as claimed in claim 1, wherein the catalyst further comprises from 1-5 weight % of an alkali metal.

7. The interesterification process as claimed in claim 1, wherein the catalyst has a surface area less than 20 m$^2$/g.

8. The interesterification process as claimed in claim 1, wherein the interesterification takes place at a temperature between 0 and 300° C.

9. The interesterification process as claimed in claim 1, wherein the catalyst is separated from the second ester mixture and added to a first ester mixture for use in a subsequent process.

10. The interesterification process according to claim 1 wherein said catalyst comprises from 30-60 weight % of calcium oxide, from 40-70 weight % of magnesium oxide and from 0 to 5 weight % of sodium or potassium.

11. The interesterification process as claimed in claim 2, wherein at least one of the starting ester compounds comprises an ester of a carboxylic acid containing from 12 to 24 carbon atoms.

12. The interesterification process as claimed in claim 2, wherein the catalyst is pre-dispersed in at least one of said starting ester compounds.

\* \* \* \* \*